(12) United States Patent
Jones

(10) Patent No.: US 11,491,103 B1
(45) Date of Patent: Nov. 8, 2022

(54) HAIR GROWTH FORMULA

(71) Applicant: Mahisha Jones, Avondale Estates, GA (US)

(72) Inventor: Mahisha Jones, Avondale Estates, GA (US)

( * ) Notice: Subject to any disclaimer, the term of this patent is extended or adjusted under 35 U.S.C. 154(b) by 0 days.

(21) Appl. No.: 16/919,776

(22) Filed: Jul. 2, 2020

(51) Int. Cl.
| | |
|---|---|
| *A61K 8/9789* | (2017.01) |
| *A61K 8/9794* | (2017.01) |
| *A61Q 7/00* | (2006.01) |
| *A61K 8/9717* | (2017.01) |
| *A61K 8/73* | (2006.01) |
| *A61K 8/49* | (2006.01) |
| *A61K 8/98* | (2006.01) |
| *A61K 8/92* | (2006.01) |
| *A61K 8/34* | (2006.01) |

(52) U.S. Cl.
CPC ............ *A61K 8/9789* (2017.08); *A61K 8/345* (2013.01); *A61K 8/4946* (2013.01); *A61K 8/73* (2013.01); *A61K 8/92* (2013.01); *A61K 8/9717* (2017.08); *A61K 8/9794* (2017.08); *A61K 8/987* (2013.01); *A61K 8/988* (2013.01); *A61Q 7/00* (2013.01)

(58) Field of Classification Search
CPC ..................................................... A61Q 7/00
See application file for complete search history.

(56) References Cited

U.S. PATENT DOCUMENTS

| | | | | |
|---|---|---|---|---|
| 2019/0000748 | A1* | 1/2019 | Carvalh Es Lago | .. A61K 8/922 |
| 2019/0133904 | A1* | 5/2019 | Tanaka | ..................... A61Q 7/00 |
| 2019/0133910 | A1* | 5/2019 | Williams | ................. A61Q 5/00 |
| 2019/0167763 | A1* | 6/2019 | Khorakiwala | ........... A61K 9/10 |
| 2019/0216707 | A1* | 7/2019 | Sung | ..................... A61K 8/9789 |

FOREIGN PATENT DOCUMENTS

| | | | | |
|---|---|---|---|---|
| EP | 0498924 | A1 * | 8/1992 | ........... A61K 8/9794 |
| FR | WO1994023689 | A1 * | 10/1994 | |
| JP | 2002370942 | A * | 12/2002 | |

OTHER PUBLICATIONS

EP-0498924-A1 translated doc (Year: 1992).*
JP-2002370942-A translated doc (Year: 2002).*
WO1994023689A1 translated doc (Year: 1994).*
Cirlini et al. (Phenolic and Volatile Composition of a Dry Spearmint (*Mentha spicata* L.) Extract, pp. 1-15, Molecules, Aug. 3, 2016) (Year: 2016).*

* cited by examiner

*Primary Examiner* — Terry A McKelvey
*Assistant Examiner* — Jacob A Boeckelman
(74) *Attorney, Agent, or Firm* — Kilpatrick Townsend & Stockton LLP

(57) ABSTRACT

A hair growth formula. This formula is natural and has proven to help hair growth or regrowth. The formula may be used on balding spots, receding hairlines, to encourage hair thickness, or anywhere hair would normally grow but is thinning or bare.

7 Claims, No Drawings

HAIR GROWTH FORMULA

FIELD OF THE DISCLOSURE

The field of this disclosure relates to a formula that helps encourage hair growth or regrowth. The formula may be used on balding spots, receding hairlines, to encourage hair thickness, or anywhere hair would normally grow but is thinning or bare.

BACKGROUND

Many people struggle with hair loss from various conditions. For example, some people who experience alopecia suffer from spot baldness, in which hair is lost from some or all areas of the body. Often, this condition results in bald spots on the scalp, typically about the size of a coin. Other people experience thinning hair for other reasons, such as stress, age, pulling, tight hair styles such as braids, or a myriad of other reasons.

These types of hair loss can erode confidence and otherwise create distress for the patient. Some hair loss treatments are highly chemical and may not always be tolerated well. Accordingly, improvements and safer formulations are desirable.

SUMMARY

Accordingly, the present inventor has developed a hair growth formula. This formula is natural and has proven to help hair growth or regrowth. Further features are described herein.

The terms "invention," "the invention," "this invention" "the present invention," "disclosure," "the disclosure," and "the present disclosure," used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

According to certain embodiments of this disclosure, there may be provided various types of hair growth formulas, depending upon the user's particular needs. There is provided an oil-based formula, a leave-in spray formula, or an edge control gel formula.

DETAILED DESCRIPTION

The described embodiments provide a natural hair growth formula. The formulas may be provided as an oil, as a liquid to be delivered as a leave in treatment spray, to be mixed with a conditioner, or any other appropriate delivery format. Although the below examples are described as either oil, spray, or gel, it should be understood that components in the various formulas made modified, mixed, or otherwise interchanged in order to change the primary delivery method. For example, the oil formula may be watered down or otherwise liquefied and delivered as a spray. The leave-in spray formula maybe be thickened for delivery as an oil or gel treatment, and so forth. The formulas described are intended to be safe enough for use on all ages (babies, children, adults, elderly), pets, or any other species that may experience unwanted hair loss.

In a specific embodiment, the treatment may be oil-based. In the oil-based formula, the components may include a combination of various seed powders, liquid extracts, natural oils, or any combination thereof. One exemplary formula combines ground fenugreek seeds, onion powder, Nettle leaf powder, orange peel powder, ground rosemary, lavender flowers, spearmint leaves, coconut oil, olive oil, castor oil, and glycerin. This formula may also incorporate ground saffron, licorice root powder, and/or coconut milk powder. In instances where ground powders are described, it is also possible to use fresh herbs, extracted liquids, or other natural compositions. In instances where seeds or fresh leaves are described, it is also possible to use powdered or dried substances, pressed herb for liquids, or other forms of the component.

The formula may be carried via glycerin or other thickening agent or natural humectant as a carrier. A specific formula incorporates:

2-3 teaspoons of ground Fenugreek
1 pound Fenugreek seeds soaked overnight in coconut oil or organic oil
2-3 teaspoons Onion power
2-3 teaspoons Nettle leaf powder
2-3 teaspoons Orange peel powder
2-3 teaspoons ground rosemary
2-3 lavender flowers
2-10 spearmint leaves
1-2 oz Olive oil
2.5 oz Castor oil
4 oz glycerin
2-3 teaspoons licorice root powder
¼ pd of irish sea moss Additions or deletions to this formula are possible and considered within the scope of this disclosure.

An alternate embodiment may also add:
2-3 teaspoons ground saffron
2-3 teaspoons coconut milk powder It should be understood that the above proportions may be modified (increased or decreased) fractional amounts in order to make larger or smaller batches of formula. It should also be understood that slight changes to the formula ingredient amounts are not expected to materially alter the effectiveness of the resulting solution. These proportions are provided for enablement and as one example only. Other options are possible and considered within the scope of this disclosure.

The above proportions are generally envisioned sufficient to make a 6-8 oz bottle of formula. The bottle may be a squeeze bottle for ease of application. The fenugreek seeds and/or powder may be soaked in coconut oil overnight to soften the seeds and release their beneficial chemicals. Then the oil from the seeds may be mixed with the other oils. The powders and oils may be combined and the lavender flowers and spearmint leaves may be allowed to infuse into the powder/oil combination. It is possible for the products to be sold with the flowers and leaves present in the product, such that they continue to infuse. This may also add an elegant and natural look and feel to the product. It is also possible for the flowers and leaves to be removed from the product prior to packaging and/or use.

Another embodiment provides a leave-in treatment spray. This formula may use water, distilled water, saline, witch hazel, rose water, or any other appropriate liquid as a carrier. In a specific example, the liquid formula comprises distilled water, rose water, fenugreek seeds soaked in rose water, hair tonic, a bacteria inhibitor or preservative, such as germaben, and glycerin or other thickening agent or natural humectant as a carrier. A specific formula incorporates:

½ cup distilled water
½ cup rose water
1.5 oz of fenugreek seeds (soaked in distilled water or rose water or both)
1 dropper full of hair tonic
1 to 2 teaspoons glycerin
Germaben II (or other anti-bacterial agent or preservative)

It should be understood that the above proportions may be modified (increased or decreased) fractional amounts in order to make larger or smaller batches of formula. It should also be understood that slight changes to the formula ingredient amounts are not expected to materially alter the effectiveness of the resulting solution. These proportions are provided for enablement and as one example only. Other options are possible and considered within the scope of this disclosure.

The above proportions are generally envisioned sufficient to make a 6-8 oz bottle of formula. The bottle may be a spray bottle for ease of application. The fenugreek seeds and/or powder may be soaked in the liquids overnight to soften the seeds and release their beneficial chemicals. Then the liquid from the seeds may be mixed with the other liquids.

A further embodiment provides an edge control formula. This can be useful to smooth/tame fly away hair or breaking hairs that make a hairstyle look less polished. Edge control can be particularly useful in a humid environment. The below edge control formula can be a wax, a gel, or a cream-like formula that can be applied directly to the hair, typically via the user's hands or via a smooth spatula/paddle. In one example, the edge control formula may be flaxseed gel, hair tonic, honey, besswax, glycerin, lavender oil, and tea tree oil. The formula may be carried via honey, beeswax, glycerin or other thickening/viscous agent or natural humectant as a carrier. A specific formula incorporates:

½ cup of flaxseed gel infused with tonic
2 tablespoons oil hair tonic
2 tablespoons of raw honey
2 tablespoons of beeswax
1 teaspoon of vegetable glycerin
15 drops of lavender oil/tea tree oil (which may be provided in any combination, but in one example, may be about 7 drops of each)
An alternate embodiment may also add:
½ teaspoon xanthum gum The components may be mixed and packaged in a small pot. It should be understood that the above proportions may be modified (increased or decreased) fractional amounts in order to make larger or smaller batches of formula. It should also be understood that slight changes to the formula ingredient amounts are not expected to materially alter the effectiveness of the resulting solution. These proportions are provided for enablement and as one example only. Other options are possible and considered within the scope of this disclosure.

The subject matter of certain embodiments of this disclosure is described with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

It should be understood that different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

What is claimed is:

1. A hair growth formula, consisting essentially of:
   ground fenugreek or fenugreek seeds or both;
   onion power;
   nettle leaf powder;
   orange peel powder;
   ground rosemary;
   lavender flowers;
   spearmint leaves;
   one or more of coconut oil; olive oil; castor oil; and glycerin,
   wherein the formula is combined into a gel for delivery.

2. The formula of claim 1, comprising fenugreek seeds soaked in olive oil.

3. The formula of claim 1, wherein proportions are about:
   2-3 teaspoons of ground Fenugreek or Fenugreek seeds soaked overnight in coconut oil or organic oil;
   2-3 teaspoons Onion power;
   2-3 teaspoons Nettle leaf powder;
   2-3 teaspoons Orange peel powder;
   2-3 teaspoons ground rosemary;
   2-3 lavender flowers;
   2-10 spearmint leaves;
   1-2 oz Olive oil;
   2. 5 oz Castor oil; and
   4 oz glycerin,
   wherein proportions may be increased or decreased fractional amounts in order to make larger or smaller batches of formula.

4. The formula of claim 1, further comprising ground saffron, coconut milk powder, or any combination thereof.

5. The formula of claim 1, further comprising xanthum gum.

6. The formula of claim 1, further comprising licorice root powder, or irish sea moss, or any combination thereof.

7. The formula of claim 6, wherein proportions are about:
   2-3 teaspoons licorice root powder;
   ¼ pd of irish sea moss,
   wherein proportions may be increased or decreased in fractional amounts in order to make larger or smaller batches of formula.

* * * * *